United States Patent
Kittaka et al.

(10) Patent No.: US 11,219,252 B2
(45) Date of Patent: Jan. 11, 2022

(54) COOLING GARMENT COOLING DEVICE AND COOLING GARMENT HAVING THE SAME MOUNTED THERETO

(71) Applicant: SUN-S Co., Ltd., Fukuyama (JP)

(72) Inventors: Kaoru Kittaka, Fukuyama (JP); Yoko Okamoto, Fukuyama (JP); Haruki Yoshimitsu, Fukuyama (JP)

(73) Assignee: SUN-S Co., Ltd., Fukuyama (JP)

( * ) Notice: Subject to any disclaimer, the term of this patent is extended or adjusted under 35 U.S.C. 154(b) by 62 days.

(21) Appl. No.: 16/622,072

(22) PCT Filed: Feb. 7, 2019

(86) PCT No.: PCT/JP2019/004467
§ 371 (c)(1),
(2) Date: Dec. 12, 2019

(87) PCT Pub. No.: WO2019/159812
PCT Pub. Date: Aug. 22, 2019

(65) Prior Publication Data
US 2020/0178621 A1    Jun. 11, 2020

(30) Foreign Application Priority Data
Feb. 15, 2018    (JP) .............................. JP2018-025117

(51) Int. Cl.
*A41D 13/005*    (2006.01)
*F25B 19/00*    (2006.01)

(52) U.S. Cl.
CPC .......... *A41D 13/0053* (2013.01); *F25B 19/00* (2013.01)

(58) Field of Classification Search
CPC ................................................ A41D 13/0053
(Continued)

(56) References Cited

U.S. PATENT DOCUMENTS 3,610,323 A * 10/1971 Troyer ............... A41D 13/0053
165/46
4,118,946 A * 10/1978 Tubin ...................... F25B 19/00
165/46
(Continued)

FOREIGN PATENT DOCUMENTS

CN    107668803 A    2/2018
JP    5-24076 U    3/1993
(Continued)

OTHER PUBLICATIONS

First Office Action dated Nov. 30, 2020 from the China National Intellectual Property Administration Machine in CN Application No. 201980002970.6 Translation.
(Continued)

*Primary Examiner* — Gloria M Hale
(74) *Attorney, Agent, or Firm* — Sughrue Mion, PLLC

(57) ABSTRACT

A cooling garment cooling device includes: a water delivery hose with a cooling water supply portion and cooling water branch portion; a pump supplying cooling water from the cooling water supply portion toward the cooling water branch portion; and plural branched water hoses having a first end-side water supply portion and second end-side water supply portion coupled to the cooling water branch portion. A portion of the branched water hoses between the first end-side water supply portion and second end-side water supply portion serves as a water outlet portion. Each branched water hose diameter is smaller than the water delivery hose diameter. The outer peripheral portion of the water outlet portion of each branched water hose orthogonal to the longitudinal direction of the branched water hose has plural water passage holes with opening areas smaller than those of the first end-side water supply portion and second end-side water supply portion.

9 Claims, 8 Drawing Sheets

(58) Field of Classification Search
USPC .............................................................. 2/458
See application file for complete search history.

(56) References Cited

U.S. PATENT DOCUMENTS

| | | | |
|---|---|---|---|
| 5,438,707 A * | 8/1995 | Horn ................... | A41D 13/0053 2/457 |
| 5,755,110 A * | 5/1998 | Silvas ................. | A41D 13/0053 165/46 |
| 2005/0088753 A1* | 4/2005 | Shimizu ............. | H01L 27/14627 359/626 |
| 2010/0011491 A1* | 1/2010 | Goldmann ........... | A41D 13/002 2/458 |
| 2010/0031428 A1 | 2/2010 | Paull | |
| 2010/0223943 A1* | 9/2010 | Loukaides .......... | A41D 13/0053 62/259.3 |
| 2010/0319381 A1* | 12/2010 | Hubler ...................... | F28D 5/00 62/259.3 |
| 2012/0227432 A1* | 9/2012 | Creech ................ | A41D 13/0053 62/259.3 |
| 2016/0206018 A1* | 7/2016 | Barbret .............. | A41D 13/0053 |

FOREIGN PATENT DOCUMENTS

| | | |
|---|---|---|
| JP | 2017-20140 A | 1/2017 |
| JP | 6284090 B1 | 2/2018 |

OTHER PUBLICATIONS

International Search Report for PCT/JP2019/004467 dated Mar. 26, 2019.

* cited by examiner

COOLING GARMENT COOLING DEVICE AND COOLING GARMENT HAVING THE SAME MOUNTED THERETO

CROSS REFERENCE TO RELATED APPLICATIONS

This application is a National Stage of International Application No. PCT/JP2019/004467 filed Feb. 7, 2019, claiming priority based on Japanese Patent Application No. 2018-025117, filed Feb. 15, 2018.

TECHNICAL FIELD

The present invention relates to a cooling garment cooling device and a cooling garment having the same mounted thereto.

BACKGROUND ART

There is proposed a cooling garment that can cool a body without the assumption that a wearer sweats.

Specifically, a water storage tank is mounted on a shoulder, and one end of a water delivery hose is connected to the water storage tank. Then, a middle portion of the water delivery hose meanders in the body portion, and the other end of the water delivery hose is connected to the water storage tank.

In addition, a pump is provided in the water delivery hose. The pump is driven to circulate cooling water in the water storage tank from the water storage tank, through the one end, the middle portion, and the other end of the water delivery hose, and back into the water storage tank (Patent Document 1 mentioned below describes a similar device).

CITATION LIST

Patent Literature

PTL 1: Japanese Unexamined Patent Application Publication No. 2017-20140

SUMMARY OF INVENTION

Technical Problem

In the configuration described above, the water delivery hose is formed with water passage holes arranged at predetermined intervals from one end toward the other end.

Thus, when a part of the cooling water flows out through the water passage holes of the water delivery hose to wet the garment and air passes through the wet portion of the garment with the pump driven to circulate the cooling water in the water storage tank through the one end, the middle portion, and the other end of the water delivery hose and back into the water storage tank, vaporization heat can be removed to cool the body as a result.

That is, the cooling water which flows out through the water passage holes of the water delivery hose can be vaporized to cool the body using the vaporization heat without the assumption that the wearer sweats.

With such a configuration according to the related art, however, a circulation path (the water storage tank, the one end, the middle portion, and the other end of the water delivery hose, and the water storage tank) is formed through the water delivery hose with the one end and the other end thereof connected to the water storage tank. Thus, a large load is imposed on the pump, which consumes significant power.

If the opening area of the water passage holes of the water delivery hose is increased, a large amount of the cooling water in the water storage tank flows out through the water passage holes of the water delivery hose, as a result of which cooling operation cannot be performed for a long time. Thus, the opening area of the water passage holes should be reduced. In order to cause a part of the circulating water to flow out through such small water passage holes, however, it is required to raise the pressure of the pump, which also increases the power consumption of the pump.

If the pressure of the pump is high and the opening area of the water passage holes is small, the cooling water jets out of the water delivery hose through the water passage holes, and preferable cooling operation may not be performed.

It is therefore an object of the present invention to suppress the power consumption of a pump.

Solution to Problem

In order to achieve the foregoing object, the present invention provides a cooling garment cooling device including: a water delivery hose provided with a cooling water supply portion and a cooling water branch portion; a pump that supplies cooling water from the cooling water supply portion toward the cooling water branch portion of the water delivery hose; and a plurality of branched water hoses each having a first end-side water supply portion and a second end-side water supply portion coupled to the cooling water branch portion of the water delivery hose, a portion of the branched water hoses between the first end-side water supply portion and the second end-side water supply portion serving as a water outlet portion, in which a diameter of each of the branched water hoses is smaller than a diameter of the water delivery hose, and an outer peripheral portion of the water outlet portion of each of the branched water hoses which is orthogonal to a longitudinal direction of the branched water hose is formed with a plurality of water passage holes, an opening area of which is smaller than an opening area of the first end-side water supply portion and the second end-side water supply portion of the branched water hose.

The cooling water supply portion is provided on a first end side of the water delivery hose, and the cooling water branch portion is provided on a second end side of the water delivery hose.

A control portion that controls operation of the pump is connected to the pump, and an operation portion that provides an operation control instruction for the pump is connected to the control portion.

A hollow fiber membrane is used as the branched water hoses.

The present invention also provides a cooling garment to which the cooling garment cooling device described above is mounted, in which the water outlet portion of the branched water hoses is disposed as meandering.

The cooling water branch portion is disposed above the cooling water supply portion of the water delivery hose, and the water outlet portion of each of the branched water hoses is disposed below the first end-side water supply portion and the second end-side water supply portion of the branched water hose.

Advantageous Effects of Invention

With the present invention described above, it is only necessary that the pump should feed the cooling water from the cooling water supply portion to the cooling water branch portion of the water delivery hose, which can reduce power consumption.

In addition, the cooling water which is fed to the cooling water branch portion of the water delivery hose flows into the plurality of branched water hoses which are coupled to the cooling water branch portion through the first end-side water supply portion and the second end-side water supply portion of the branched water hoses, and then flows out through the plurality of water passage holes which are provided in the water outlet portion between the first end-side water supply portion and the second end-side water supply portion of each branched water hose. An appropriate amount of the cooling water can be supplied to a wide area of the body, and a high cooling effect is obtained as a result.

Further, the diameter of each branched water hose is smaller than the diameter of the water delivery hose, and the outer peripheral portion of the branched water hoses which is orthogonal to the longitudinal direction thereof is formed with the plurality of water passage holes, the opening area of which is smaller than the opening area of the first end-side water supply portion and the second end-side water supply portion of the branched water hoses. Thus, the cooling water which flows out of the branched water hoses percolates over a wide range and in a small amount, and thus the user can be cooled comfortably without feeling significantly wet at a part of his/her body.

In the present invention, in addition, the first end-side water supply portion and the second end-side water supply portion of each branched water hose are coupled to the cooling water branch portion of the water delivery hose, and thus the cooling water is supplied to the water outlet portion from both the first end-side water supply portion and the second end-side water supply portion of each branched water hose. As a result, even if the branched water hoses are partly clogged, the first end-side water supply portion side of the clogged portion is supplied with the cooling water from the first end-side water supply portion side, and the second end-side water supply portion side of the clogged portion is supplied with the cooling water from the second end-side water supply portion side.

That is, even if the branched water hoses are partly clogged because of a long period of use etc., the first end-side water supply portion side of the clogged portion is supplied with the cooling water from the first end-side water supply portion side, and the second end-side water supply portion side of the clogged portion is supplied with the cooling water from the second end-side water supply portion side, which allows exhibiting a stable cooling effect over a long period.

DESCRIPTION OF EMBODIMENTS

First Embodiment

An embodiment of the present invention will be described below with reference to the accompanying drawings.

Figure 1:
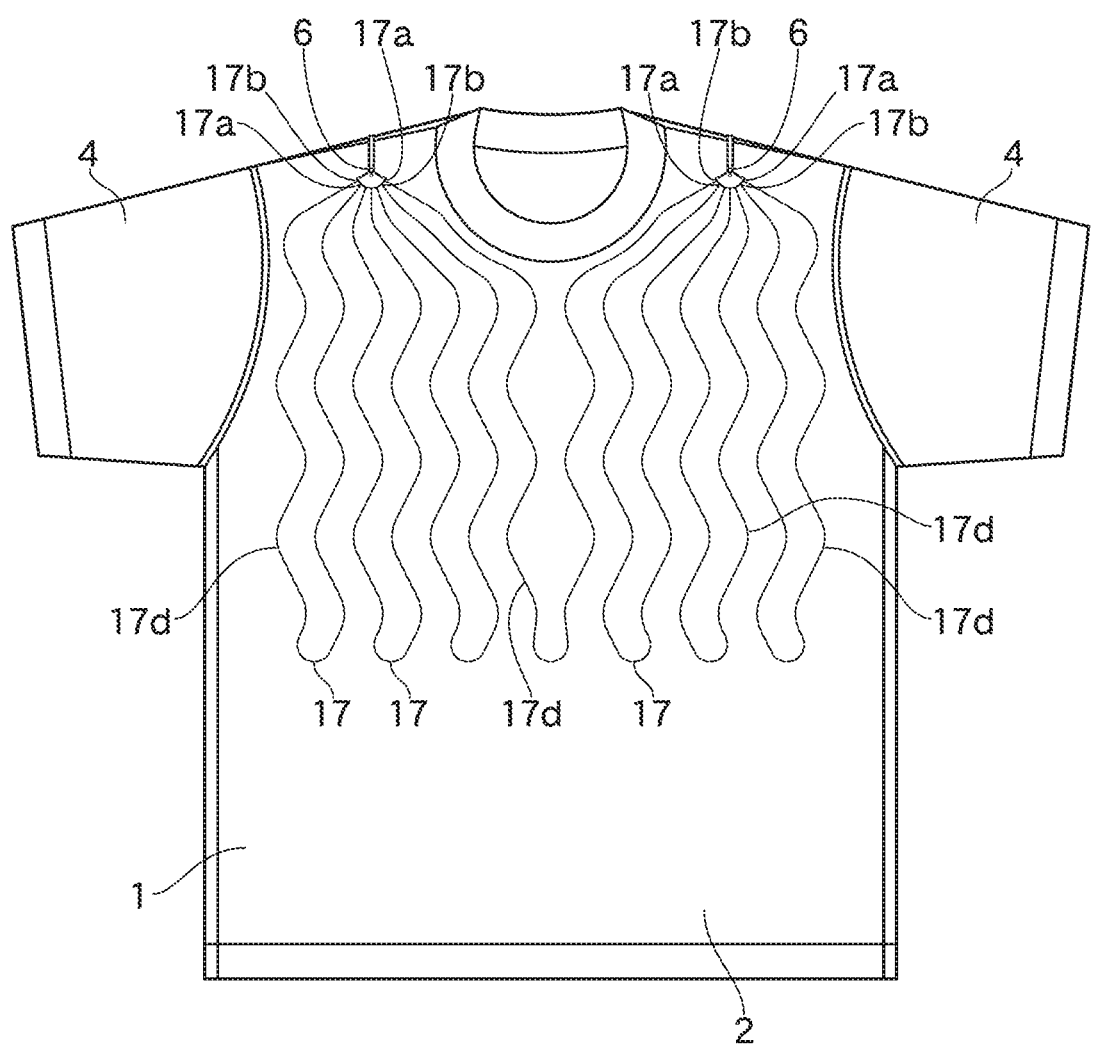
FIG. 1 is a front view of a cooling garment that has a cooling garment cooling device according to an embodiment of the present invention mounted thereto.
Figure 2:
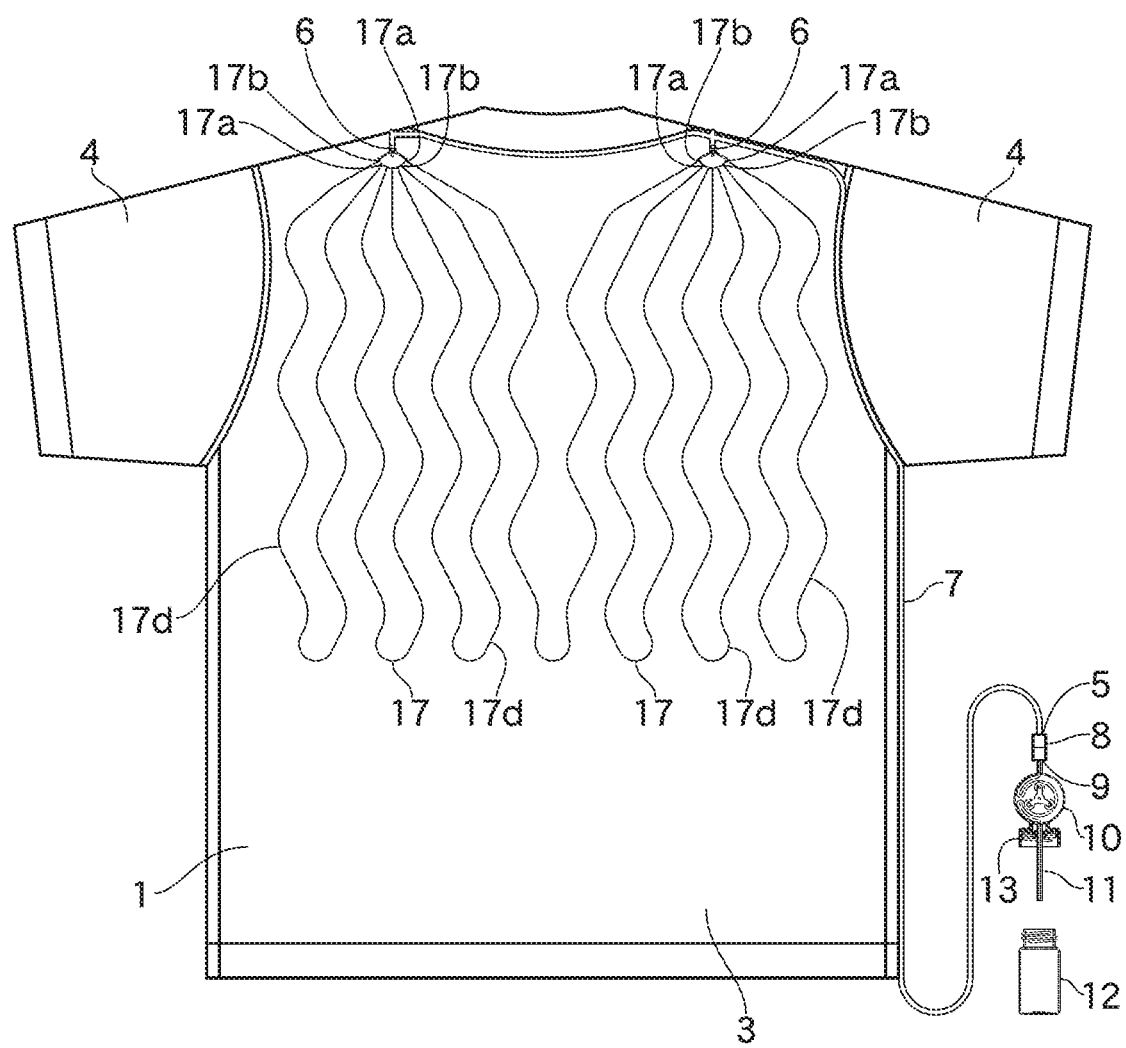
FIG. 2 is a rear elevation view of the cooling garment.

FIG. 1 is a front view of a cooling garment that has a cooling garment cooling device according to the present embodiment mounted thereto. FIG. 2 is a rear elevation view of the cooling garment.

In FIGS. 1 and 2, reference numeral 1 denotes a cooling garment, which is composed of a front surface clothing material 2, a back surface clothing material 3, and right and left sleeves 4.

A water delivery hose 7 provided with a cooling water supply portion 5 and a cooling water branch portion 6 is mounted at a side portion of the back surface clothing material 3 to extend in the vertical direction.

Specifically, the cooling water supply portion 5 extends to the lower portion of the cooling garment 1, and then extends to the outside of the cooling garment 1. A coupler 8 is mounted to the extended portion of the cooling water supply portion 5.

The cooling water branch portion 6 is provided on the side of the other end of the water delivery hose 7. In the present embodiment, the water delivery hose 7 is branched on the side of the other end, and the cooling water branch portion 6 is disposed at a total of four locations, namely the right and left upper portions of the front surface clothing material 2 of the cooling garment 1 and the right and left upper portions of the back surface clothing material 3 of the cooling garment 1.

The coupler 8, which is coupled to the cooling water supply portion 5 of the water delivery hose 7, is connected to a pump 10 and a water supply pipe 11 via a coupler 9. The water supply pipe 11 is inserted into a drinking water bottle 12 which is commercially available, for example. By threadably engaging the cap portion 13 with the drinking water bottle 12 by turning the cap portion 13 in that state, the water supply pipe 11 and the pump 10 are fixed to the drinking water bottle 12.

Figure 9:
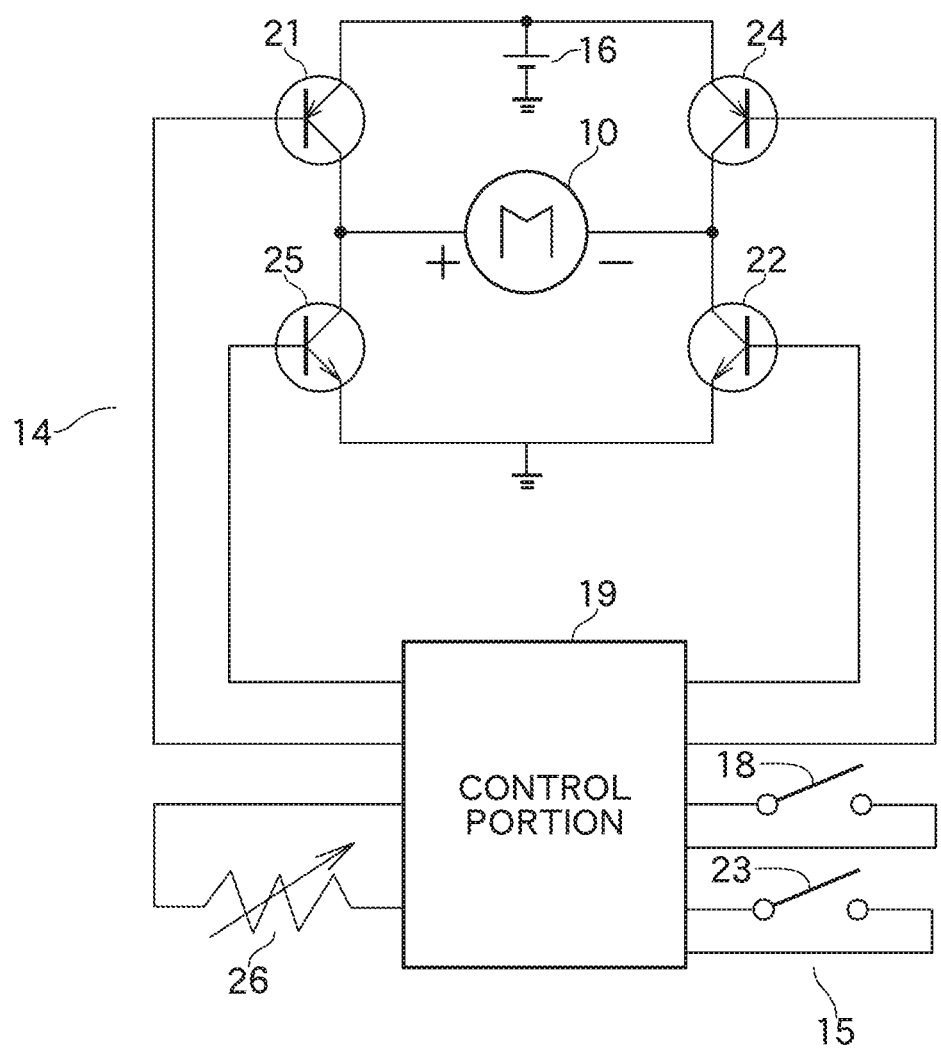
FIG. 9 is a control block diagram of the cooling garment cooling device mounted to the cooling garment.

The pump 10 is provided with a control circuit portion 14, an operation portion 15, and a battery 16 illustrated in FIG. 9 so that the pump 10 can be started and stopped and the operation amount of the pump 10 can be controlled by operating the operation portion 15.

That is, cooling water can be supplied by the pump 10 from the cooling water supply portion 5 toward the cooling water branch portions 6 of the water delivery hose 7.

Returning to the description of FIGS. 1 and 2, a plurality of branched water hoses 17 is coupled to the four cooling water branch portions 6 of the water delivery hose 7.

This respect will be described in further detail. A first end-side water supply portion 17a and a second end-side water supply portion 17b of the plurality of branched water hoses 17 are coupled to the four cooling water branch portions 6 of the water delivery hose 7.

That is, the diameter of the branched water hoses 17 is smaller than the diameter of the water delivery hose 7, and thus the first end-side water supply portion 17a and the second end-side water supply portion 17b of the plurality of branched water hoses 17 can be coupled to the four cooling water branch portions 6 of the water delivery hose 7.

Figure 3:
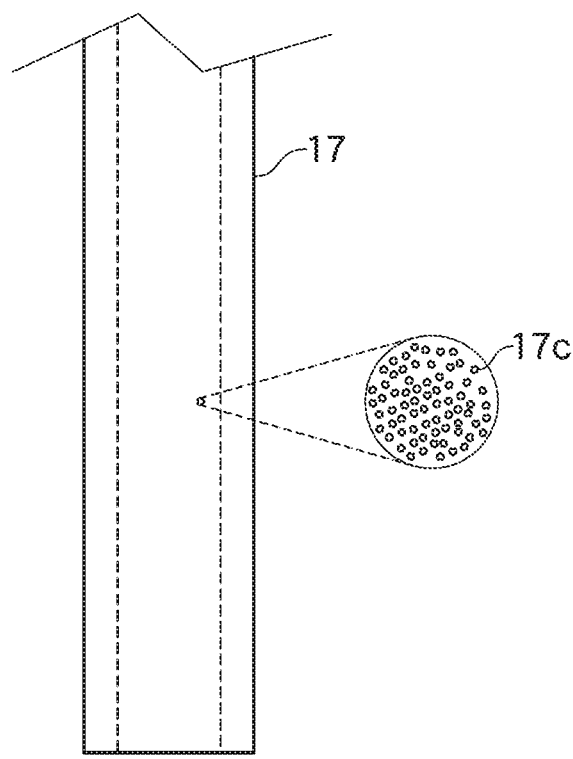
FIG. 3 is a plan view of a branched water hose mounted to the cooling garment.
Figure 4:
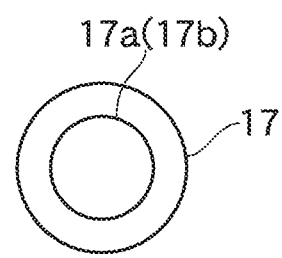
FIG. 4 is a side view of the branched water hose mounted to the cooling garment.

The branched water hoses 17 are formed from a hollow fiber membrane. As illustrated in FIGS. 3 and 4, the outer peripheral portion of the branched water hoses 17 which is orthogonal to the longitudinal direction thereof is formed with a plurality of water passage holes 17c, the opening area of which is smaller than the opening area of the first end-side water supply portion 17a and the second end-side water supply portion 17b of the branched water hoses 17.

That is, the first end-side water supply portion 17a and the second end-side water supply portion 17b of the branched water hoses 17 are coupled to the cooling water branch portions 6 of the water delivery hose 7 as discussed above, and the cooling water which is supplied through the first end-side water supply portion 17a and the second end-side water supply portion 17b flows out of the branched water hoses 17 through the water passage holes 17c.

That is, a portion of the branched water hoses 17, which are formed from the hollow fiber membrane, between the first end-side water supply portion 17a and the second end-side water supply portion 17b serves as a water outlet portion 17d of the branched water hoses 17, and the entire surface of the cooling garment 1 can be supplied with the cooling water since the water outlet portion 17d is disposed as meandering in the front surface clothing material 2 and the back surface clothing material 3.

The branched water hoses 17 will be further described. A hollow fiber membrane with an outer dimension of 0.5 mm is used as the branched water hoses 17, and the outer peripheral surface of the branched water hoses 17 is provided with numberless water passage holes 17c with an opening diameter of 0.4 microns or less.

Further specifically, as illustrated in FIG. 3, the water passage holes 17c which are provided in the outer peripheral portion of the branched water hoses 17 are independent of the other adjacent water passage holes 17c in the outer circumferential direction of the branched water hoses 17, but at least partially overlap such adjacent water passage holes 17c in the longitudinal direction of the branched water hose 17. That is, the hollow fiber membrane is formed with numberless water passage holes 17c.

In the present embodiment, this state is expressed as the outer peripheral portion of the branched water hoses 17 which is orthogonal to the longitudinal direction thereof being formed with the plurality of water passage holes 17c, the opening area of which is smaller than the opening area of the first end-side water supply portion 17a and the second end-side water supply portion 17b of the branched water hoses 17, as discussed above.

Such use of the hollow fiber membrane, which is generally used as a liquid filter, as the branched water hoses 17 is one characteristic of the present embodiment.

In the present embodiment, the cooling water supply portion 5 of the water delivery hose 7 is disposed at the lower part of the cooling garment 1, the cooling water branch portions 6 are disposed at the upper part of the cooling garment 1, and the first end-side water supply portion 17a and the second end-side water supply portion 17b of the branched water hoses 17 are coupled to the cooling water branch portions 6 disposed at the upper part of the cooling garment 1. Thus, the water outlet portion 17d is disposed, as meandering in the cooling garment 1, below at the part lower than the part in which the first end-side water supply portion 17a and the second end-side water supply portion 17b are coupled.

Next, the pump 10 will be described.

The pump 10 is rotated forward via switching elements 21 and 22 by a control portion 19 when a switch 18 of the operation portion 15 for forward rotation is closed. Conversely, the pump 10 is rotated in reverse via switching elements 24 and 25 by the control portion 19 when a switch 23 of the operation portion 15 for reverse rotation is closed.

The intensity of the forward rotation and the reverse rotation is adjusted using a volume 26 of the operation portion 15.

That is, the amount of power supplied to the pump 10 can be adjusted by adjusting the volume 26, and thus the intensity of the forward rotation and the reverse rotation can be adjusted accordingly.

In the present embodiment, in addition, sufficient cooling water percolates through the water passage holes 17c of the branched water hoses 17 even during intermittent drive of the pump 10, which can reduce the power consumption of the pump 10.

Next, a main portion of a method of manufacturing the cooling garment 1 according to the present embodiment will be described.

Figure 10:
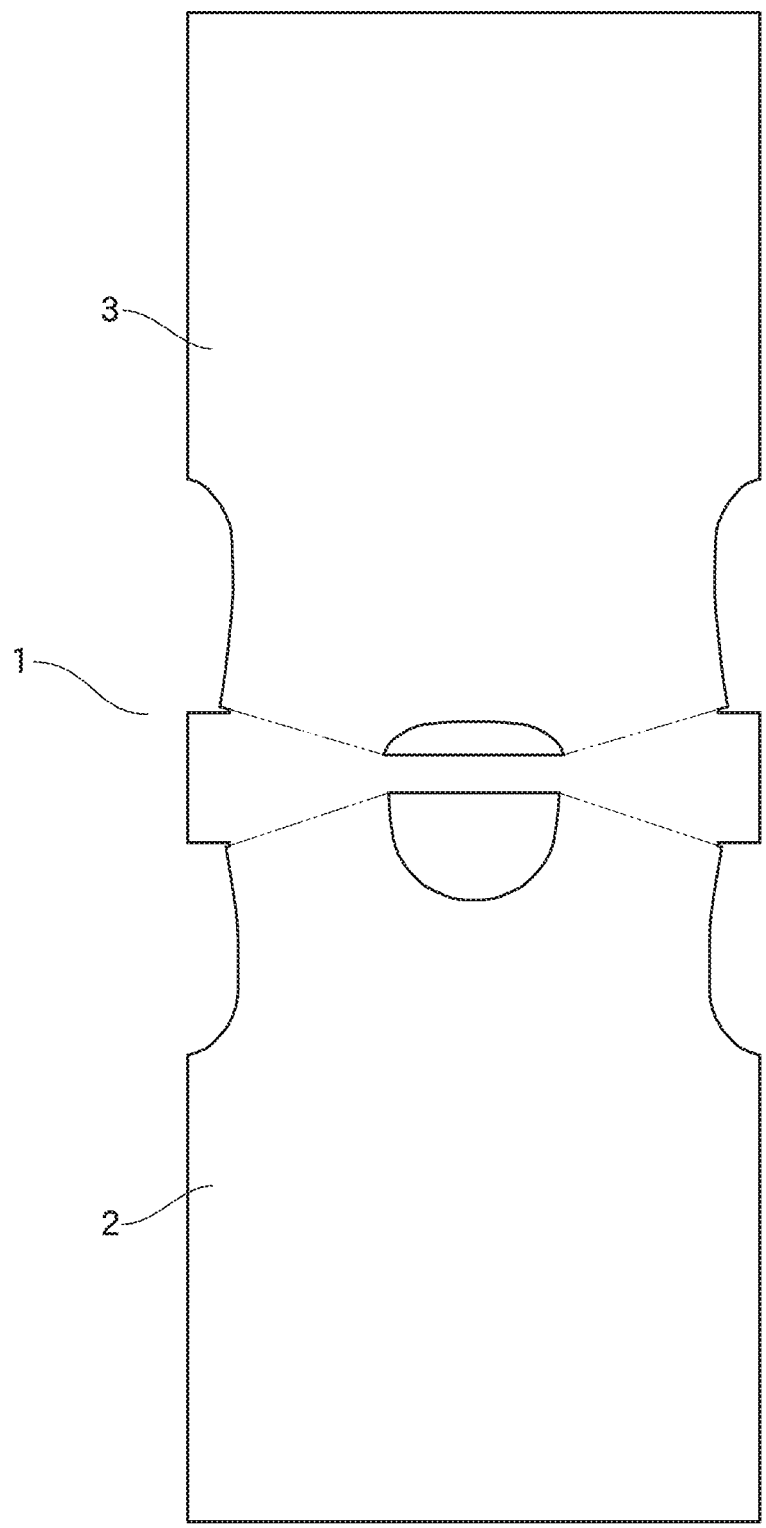
FIG. 10 is a plan view illustrating a method of manufacturing the cooling garment.

FIG. 10 illustrates a state in which the cooling garment 1 is cut into the front surface clothing material 2 and the back surface clothing material 3.

Figure 5:
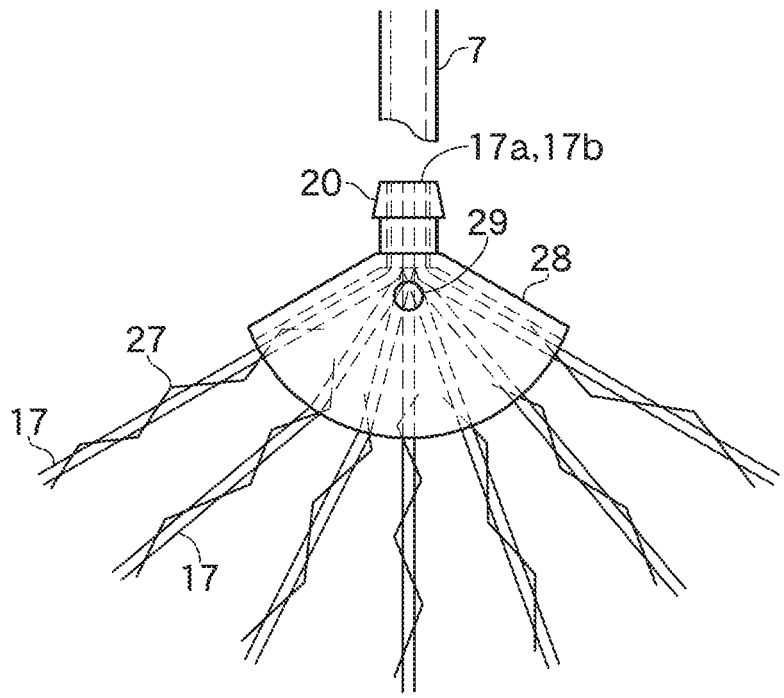
FIG. 5 is a plan view of an end portion of the branched water hose mounted to the cooling garment.
Figure 11:
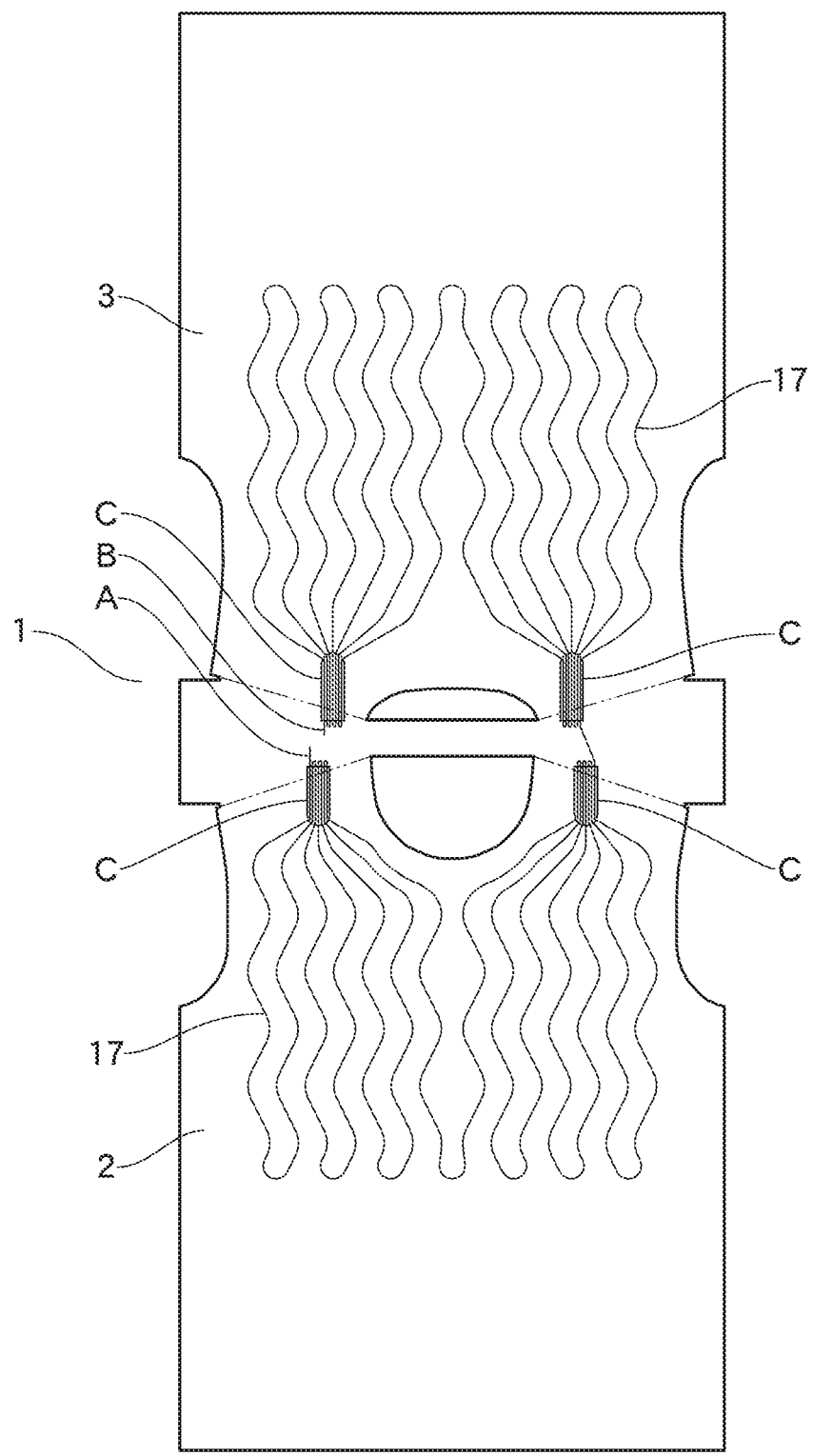
FIG. 11 is a plan view illustrating the method of manufacturing the cooling garment.

First, the branched water hose 17 in a wound state is sewn onto the upper left (A point) of the front surface clothing material 2, with the branched water hose 17 not sewn in the C area. Next, after passing through the C area, the branched water hose 17 is sewn concurrently while meandering downward, and thereafter sewn concurrently while meandering upward from below (a sewing thread 27 is illustrated in FIG. 5). This process is repeated to complete the left zone of the front surface clothing material 2 in FIG. 11, and then the process transitions to the right zone of the front surface clothing material 2 in FIG. 11.

After that, the process continuously transitions to the right zone of the back surface clothing material 3 and then transitions to the left zone of the back surface clothing material 3 to reach the B point, disposing the branched water hose 17.

That is, the branched water hose 17 is disposed unicursally from the A point to the B point, which improves the efficiency of the mounting work.

Figure 12:
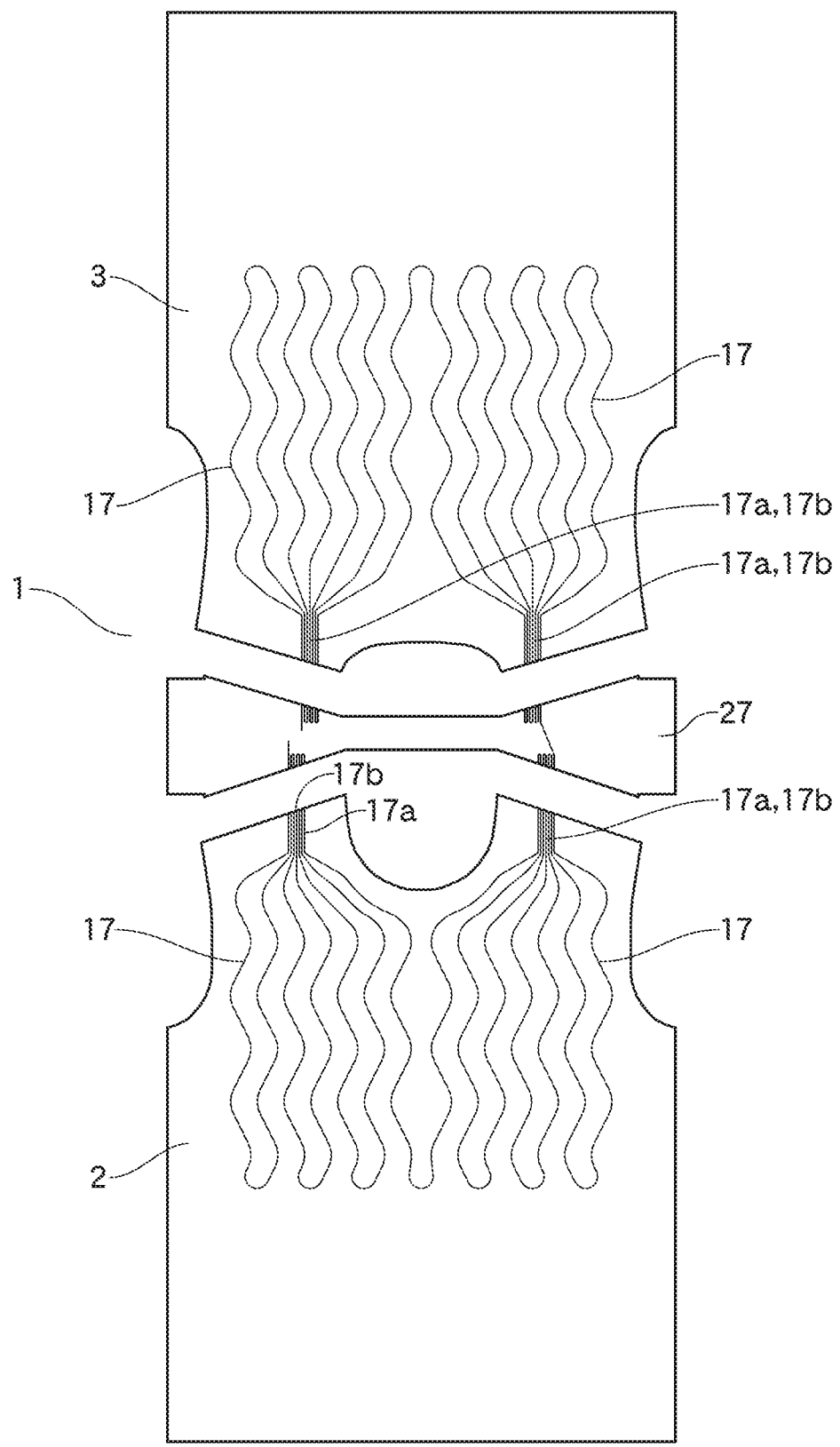
FIG. 12 is a plan view illustrating the method of manufacturing the cooling garment.

After that, when the front surface clothing material 2 and the back surface clothing material 3 are separated from each other at a coupling portion 27 as illustrated in FIG. 12, the first end-side water supply portion 17a and the second end-side water supply portion 17b of the plurality of branched water hoses 17 are present at the right and left upper portions of the front surface clothing material 2.

In addition, the first end-side water supply portion 17a and the second end-side water supply portion 17b of the plurality of branched water hoses 17 are present also at the right and left upper portions of the back surface clothing material 3.

The first end-side water supply portion 17a and the second end-side water supply portion 17b of each branched water hose 17 are not sewn onto the front surface clothing material 2 and the back surface clothing material 3, and can be moved freely.

Figure 6:
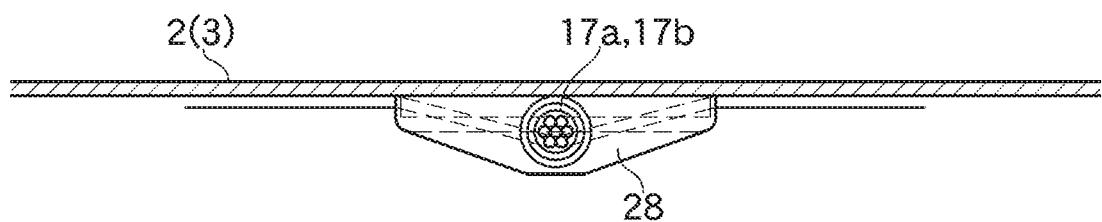
FIG. 6 is a side view of the end portion of the branched water hose mounted to the cooling garment.
Figure 7:
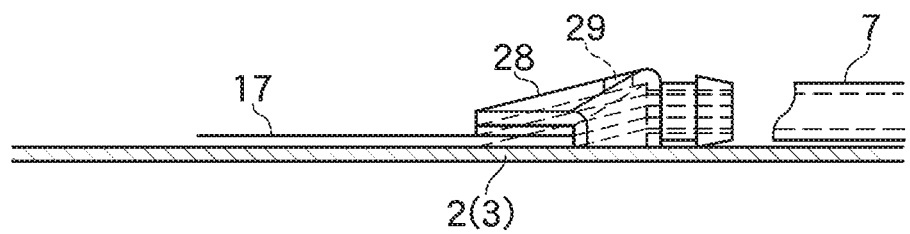
FIG. 7 is a sectional view of the end portion of the branched water hose mounted to the cooling garment.
Figure 8:
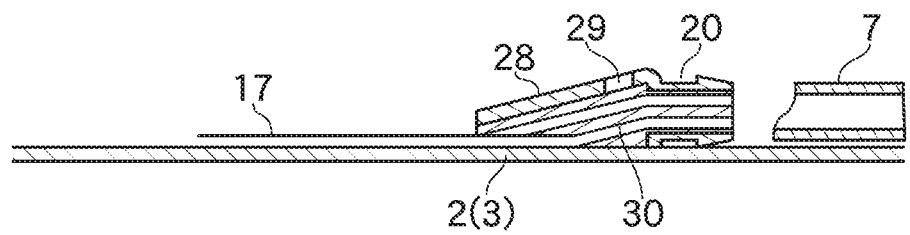
FIG. 8 is a sectional view of the end portion of the branched water hose mounted to the cooling garment.

In this state, the first end-side water supply portion 17a and the second end-side water supply portion 17b of the branched water hoses 17 are inserted into a coupler 28 as illustrated in FIGS. 5 and 6, and then an adhesive 30 is injected through an opening portion 29 of the coupler 28 as illustrated in FIGS. 7 and 8.

That is, the first end-side water supply portion 17a and the second end-side water supply portion 17b of the plurality of branched water hoses 17 are fixed to the front surface clothing material 2 and the back surface clothing material 3 together with the coupler 28 using the adhesive 30.

At this time, in order that the first end-side water supply portion 17a and the second end-side water supply portion 17b of the plurality of branched water hoses 17 are not clogged with the adhesive 30, the first end-side water supply portion 17a and the second end-side water supply portion 17b of the branched water hoses 17 are sufficiently drawn out of the coupler 28 (to the upper side in FIG. 5 or the right side in FIG. 8), and portions of the branched water hoses 17 that project from the coupling portion 20 are cut after the adhesive 30 is cured.

In addition, as discussed above, the branched water hoses 17 are formed from the hollow fiber membrane, and the water passage holes 17c in the outer peripheral surface thereof have a significantly small opening area. Thus, the adhesive 30 which is viscous does not enter the branched water hoses 17 through the water passage holes 17, and the branched water hoses 17 are not clogged at this portion.

Finally, the cooling water branch portion 6 of the water delivery hose 7 is pushed onto the outer periphery of the coupling portion 20 of the coupler 28 while being elastically deformed in FIG. 5 to couple the first end-side water supply portion 17a and the second end-side water supply portion 17b of the branched water hoses 17 to the cooling water branch portion 6 of the water delivery hose 7.

Operation of the configuration described above will be described.

First, a user wears the cooling garment 1 in FIG. 1.

Then, the water supply pipe 11 is inserted into the drinking water bottle 12 which is commercially available, for example. By threadably engaging the cap portion 13 with the drinking water bottle 12 by turning the cap portion 13 in that state, the water supply pipe 11 and the pump 10 are fixed to the drinking water bottle 12.

After that, when the switch 18 of the operation portion 15 for forward rotation is closed, the pump 10 is rotated forward via the switching elements 21 and 22 by the control portion 19. Consequently, the cooling water in the drinking water bottle 12 percolates to the front surface clothing material 2 and the back surface clothing material 3 of the cooling garment 1 via the cooling water supply portion 5 and the cooling water branch portion 6 of the water delivery hose 7 and the first end-side water supply portion 17a and the second end-side water supply portion 17b of the branched water hoses 17 and through the numberless water passage holes 17c which are formed in the water outlet portion 17d of the branched water hoses 17 which are disposed as meandering in the cooling garment 1, so that the cooling water is vaporized by the outside air, a wind, etc.

That is, the user is cooled effectively by the heat of vaporization of the cooling water in the cooling garment 1 even in a situation in which the user is not sweating.

In this manner, with the present embodiment, it is only necessary that the pump 10 should simply feed the cooling water from the cooling water supply portion 5 to the cooling water branch portions 6 of the water delivery hose 7, which can reduce power consumption.

In addition, the cooling water which is fed to the cooling water branch portions 6 of the water delivery hose 7 flows into the plurality of branched water hoses 17 which are coupled to the cooling water branch portions 6 through the first end-side water supply portion 17a and the second end-side water supply portion 17b of the branched water hoses 17, and then flows out through the plurality of water passage holes 17c which are present in the water outlet portion 17d of each branched water hose 17.

At this time, the water outlet portion 17d meanders widely in the cooling garment 1. Thus, an appropriate amount of the cooling water can be supplied to a wide area of the body, and a high cooling effect is obtained as a result.

That is, with the present embodiment, when the cooling water is fed from the cooling water supply portion 5 of the water delivery hose 7 to the cooling water branch portions 6 by the pump 10, the cooling water thereafter flows out of the branched water hoses 17 through the water passage holes 17c, which are open to the atmosphere, of the branched water hose 17 because of the gravity on the cooling water itself and the capillary action of the minute water passage holes 17c. Thus, the power consumption of the pump 10 can be suppressed.

In the present embodiment, by way of example, a 3-V battery 16 which includes two AA batteries connected in series can be used for eight hours or more.

Further, the diameter of each branched water hose 17 is smaller than the diameter of the water delivery hose 7, and the outer peripheral portion of the branched water hoses 17 which is orthogonal to the longitudinal direction thereof is formed with the plurality of water passage holes 17c, the opening area of which is smaller than the opening area of the first end-side water supply portion 17a and the second end-side water supply portion 17b of the branched water hoses 17. Thus, the cooling water which flows out of the branched water hoses 17 percolates over a wide range and in a small amount, and thus the user can be cooled comfortably without feeling significantly wet at a part of his/her body.

In the present embodiment, 500 cc of the cooling water is used per hour, depending on the environment of use. Thus, a drinking water container which is commercially available is coupled, as it is, to the cap portion 13 of the drinking water bottle 12.

When the cooling water runs out, tap water can be put into the drinking water bottle 12 to continue the use of the cooling garment 1 easily.

The switch 23 for reverse rotation is prepared in order to rotate the pump 10 in reverse and resolve a so-called air trapping state, in which the previous cooling water remains and air also exists in the branched water hose 17, in the case where the air trapping state is caused in the branched water hose 17.

In addition, the cooling garment 1 is often used in a hot outdoor environment, and the cooling garment 1 according to the present embodiment can continue continuous cooling operation even if the branched water hoses 17 are partly clogged with dust etc., for example.

That is, in the present embodiment, the first end-side water supply portion 17a and the second end-side water supply portion 17b of each branched water hose 17 are coupled to the cooling water branch portions 6 of the water delivery hose 7, and thus the cooling water is supplied to the water outlet portion 17d from both the first end-side water supply portion 17a and the second end-side water supply portion 17b of each branched water hose 17. As a result, even if the branched water hoses 17 are partly clogged, the first end-side water supply portion 17a side of the clogged portion is supplied with the cooling water from the first end-side water supply portion 17a side, and the second end-side water supply portion 17b side of the clogged portion is supplied with the cooling water from the second end-side water supply portion 17b side, which allows exhibiting a stable cooling effect over a long period.

Although an embodiment of the present invention has been described above in detail, the present invention is not limited thereto. A variety of design changes can be made to the present invention without departing from the matter defined in the claims. The present invention provides a cooling garment that is effective in a hot season for outdoor activities, outdoor operations, indoor operations in a hot environment, etc.

REFERENCE SIGNS LIST 1 cooling garment
2 front surface clothing material
3 back surface clothing material
4 sleeve
5 cooling water supply portion
6 cooling water branch portion
7 water delivery hose
8 coupler
9 coupler
10 pump
11 water supply pump
12 drinking water bottle
13 cap portion
14 control circuit portion
15 operation portion
16 battery
17 branched water hose
17a first end-side water supply portion
17b second end-side water supply portion
17c water passage hole
17d water outlet portion
18 switch
19 control portion
20 coupling portion
21 switching element
22 switching element
23 switch
24 switching element
25 switching element
26 volume
27 sewing thread
28 coupler
29 opening end
30 adhesive

The invention claimed is:

1. A cooling garment cooling device comprising:
a water delivery hose provided with a cooling water supply portion and a cooling water branch portion;
a pump that supplies cooling water from the cooling water supply portion toward the cooling water branch portion of the water delivery hose; and
a plurality of branched water hoses each having a first end-side water supply portion and a second end-side water supply portion coupled to the cooling water branch portion of the water delivery hose, a portion of the branched water hoses between the first end-side water supply portion and the second end-side water supply portion serving as a water outlet portion,
wherein a diameter of each of the branched water hoses is smaller than a diameter of the water delivery hose, and an outer peripheral portion of the water outlet portion of each of the branched water hoses which is orthogonal to a longitudinal direction of the branched water hose is formed with a plurality of water passage holes, an opening area of which is smaller than an opening area of the first end-side water supply portion and the second end-side water supply portion of the branched water hose.

2. The cooling garment cooling device according to claim 1,
wherein the cooling water supply portion is provided on a first end side of the water delivery hose, and the cooling water branch portion is provided on a second end side of the water delivery hose.

3. The cooling garment cooling device according to claim 1,
wherein a control portion that controls operation of the pump is connected to the pump, and an operation portion that provides an operation control instruction for the pump is connected to the control portion.

4. The cooling garment cooling device according to claim 1,
wherein a hollow fiber membrane is used as the branched water hoses.

5. A cooling garment to which the cooling garment cooling device according to claim 1 is mounted, wherein the water outlet portion of the branched water hoses is disposed as meandering.

6. The cooling garment according to claim 5,
wherein the cooling water branch portion is disposed above the cooling water supply portion of the water delivery hose, and the water outlet portion of each of the branched water hoses is disposed below the first end-side water supply portion and the second end-side water supply portion of the branched water hose.

7. The cooling garment cooling device according to claim 2,
wherein a control portion that controls operation of the pump is connected to the pump, and an operation portion that provides an operation control instruction for the pump is connected to the control portion.

8. The cooling garment cooling device according to claim 1,
wherein a position of the cooling water branch portion is higher than a position of the branched water hoses.

9. The cooling garment cooling device according to claim 1,
wherein the water passage holes have an opening diameter of 0.4 microns or less.

* * * * *